United States Patent
Mojsa

(10) Patent No.: US 10,905,730 B2
(45) Date of Patent: Feb. 2, 2021

(54) PHYTOCANNABINOID TOPICAL COMPOSITIONS FOR RELEIVING PAIN

(71) Applicant: Agnes V. Mojsa, Naugatuck, CT (US)

(72) Inventor: Agnes V. Mojsa, Naugatuck, CT (US)

(*) Notice: Subject to any disclaimer, the term of this patent is extended or adjusted under 35 U.S.C. 154(b) by 0 days.

(21) Appl. No.: 16/189,969

(22) Filed: Nov. 13, 2018

(65) Prior Publication Data

US 2019/0142888 A1 May 16, 2019

Related U.S. Application Data

(60) Provisional application No. 62/585,734, filed on Nov. 14, 2017.

(51) Int. Cl.
| | |
|---|---|
| *A61K 36/00* | (2006.01) |
| *A61K 36/185* | (2006.01) |
| *A61K 31/352* | (2006.01) |
| *A61K 31/05* | (2006.01) |
| *A61K 9/00* | (2006.01) |
| *A61P 29/02* | (2006.01) |
| *A61K 9/06* | (2006.01) |
| *A61K 47/44* | (2017.01) |

(52) U.S. Cl.
CPC .......... *A61K 36/185* (2013.01); *A61K 9/0014* (2013.01); *A61K 9/06* (2013.01); *A61K 31/05* (2013.01); *A61K 31/352* (2013.01); *A61P 29/02* (2018.01); *A61K 47/44* (2013.01); *A61K 2236/15* (2013.01); *A61K 2236/37* (2013.01)

(58) Field of Classification Search
None
See application file for complete search history.

(56) References Cited

U.S. PATENT DOCUMENTS

| | | | |
|---|---|---|---|
| 2012/0027701 A1* | 2/2012 | Stone ................... | A61K 9/0014 424/59 |
| 2013/0319889 A1* | 12/2013 | DeSantis ................ | A61K 8/927 206/438 |
| 2016/0235661 A1* | 8/2016 | Changoer ............ | A61K 9/0014 |

FOREIGN PATENT DOCUMENTS

| | | | | |
|---|---|---|---|---|
| WO | WO-2016092539 A1 * | 6/2016 | ........... | A61K 31/352 |

* cited by examiner

*Primary Examiner* — Qiuwen Mi
(74) *Attorney, Agent, or Firm* — Dara L. Onofrio, Esq.; Onofrio Law

(57) ABSTRACT

A topical composition for pain relief comprising phytocannabinoids and a carrier vehicle for the phytocannabinoids, which include tetrahydrocannabinol THC and cannabidiol CBD present in amounts up to 25%, delivered to a user's skin and/or lips to alleviate pain.

16 Claims, No Drawings

PHYTOCANNABINOID TOPICAL COMPOSITIONS FOR RELEIVING PAIN

This application claims the benefit of U.S. provisional application Ser. No. 62/585,734 filed Nov. 14, 2017 which is incorporated herein in its entirety by reference.

FIELD OF THE INVENTION

The present invention relates to phytocannabinoid topical compositions for relieving pain. More particularly, the invention relates to topical ointments, creams and balms including tetrahydrocannabinol ("THC") to help heal and relieve pain in individuals suffering from various ailments and disease.

BACKGROUND OF THE INVENTION

A great number of the population in the United States as well as across the globe, suffer from some kind of pain. Most individuals look to their doctor to prescribe medication to alleviate and relieve their pain. While there are also holistic and alternative methods to relieve pain such as acupuncture, massage therapy, physical therapy these must be done by third parties to an individual. There is the need for a more holistic and natural way for an individual to alleviate their pain without having to take prescription medication which comes with sometimes deadly side effects.

Phytocannabinoids are cannabinoids that occur naturally in the cannabis plant. The classical cannabinoids are formed through decarboxylation of their respective 2-carboxylic acids (2-COOH), a process which is catalyzed by heat, light or alkaline conditions. The phytocannabinoids delta-9-tetrahydrocannabinol (THCA), cannabidiol (CBD), and cannabinol (CBN) have become the most widely known for their numerous health benefits. Because of the cannabis plant's unique phytocannabinoids, the use of medicinal marijuana has become commonplace in many areas of the world as an acceptable treatment for numerous diseases and disorders.

The cannabis plant contains over 545 compounds that have been identified by researchers. Of these compounds identified approximately 113 are phytocannabinoids. The plant's phytocannabinoids all interact and bind together with the terpenes and flavonoids to produce a complex interplay within the plant's system. The cannabinoids are the most highly concentrated in the plant's resin, which is produced in its trichome glands. Different strains of cannabis contain varying levels of the different phytocannabinoids. Growers frequently cultivate marijuana plants to contain higher or lower levels of such cannabinoids, especially tetrahydrocanniabinol THC and cannabidiol CBD.

Phytocannabinoids are, for the most part, insoluble in water but are soluble in alcohols, fats, and other non-polar organic solvents.

Trichomes are the resin glands of the pot plant which contain the THC and CBD and other active medicinal cannabinoids. Extracting trichomes from the cannabis plant preserves terpenes. Terpenes are the pungent oils that give the cannabis plant its distinct tastes and smells. Terpenes also create an entourage of health benefits.

THC and other medicinal cannabinoids are only found inside the heads of three different types of trichomes: 1. Bulbous; 2. Capitate sessile; and 3. Capitate-stalked.

Bulbous trichomes appear on the surface of the entire plant but are so small (10-15 micrometers or microns) that you won't see them without the aid of a microscope. For reference, the width of a human hair is 40-50 microns.

Capitate sessile trichomes are the next largest group. They are slightly larger than bulbous trichomes and are significantly more abundant. Capitate sessile trichomes start to take on the more familiar head-and-stalk shape.

Capitate-stalked trichomes are the most common of the bunch. They range in size from 50-100 microns which means they can be seen with the naked eye. Capitate-stalked trichomes are composed of a basal cell (stalk) topped off by a waxy gland head.

It is believed that essential cannabinoids such as THC were created in the calyxes, or green plant tissue, which serve as the womb from which the mushroom shaped trichome glands grow. Scientists now observe that the trichomes themselves create the cannabinoids and terpenes. The trichomes grow from the body of the calyx, but it's the trichomes themselves that ultimately produce the cannabinoids.

The bud contains pistils which are double strands of hair that grow out of the calyx material, catch cannabis pollen from male pot plants to facilitate reproduction and flower production.

Trichomes serve as the pot plant's phalanx of little shields responsible for the developing pot plant's triumphs against fungus and pesky pot-loving insects that would otherwise destroy entire crops of cannabis plants. Trichomes are also the "sunscreen" of growing marijuana plants. Trichomes protect it from the sun's ultraviolet rays as well as high wind and low humidity. Trichomes have their own cycle of growth within the overall marijuana plant's lifecycle. The theory is that photosynthetic cannabinoid precursors are transported and transformed into THC, CBD, additional cannabinoids, and terpenes in the secretory vesicles of the trichome gland head as pictured above. Cannabinoids and terpenes accumulate between the outer cuticle of the trichome as the pot plant grow. The trichome gland head grows thicker and more bulbous as the secretory vesicles produce oil and push it towards the cuticle. The gland head eventually matures and falls off as the budding process nears completion.

Folium Biosciences in Colorado is a producer, manufacturer, and distributor of hemp derived phytocannabinoids, primarily cannabidiol (CBD) oil, which are used to make several products including gummies, edibles, lotions, balms, creams and capsules. Folium operates a phytocannabinoid extraction and purification facility which separates and removes unwanted compounds, while creating potent levels of phytocannabinoids, terpenes, terpenoids, and flavonoids.

Folium's main product, from which an array of products is made, is a phytocannabinoid rich (PCR) hemp oil that is naturally rich in Cannabidiol (CBD), and contains Cannabigerol (CBG), Cannabinol (CBN), Cannabichromene (CBC), as well as terpenes, flavonoids, and essential amino acids. However, it is noted that there is no tetrahydrocannabinol (THC) in Folium's hemp oil. Unlike the Folium's product line, the invention includes tetrahydrocannabinol (THC) which is essential to the pain-relieving characteristics of the compositions.

The purpose of the invention is to provide topical compositions including ointments, balms and creams to help manage and relieve pain in cancer patients as well as for people suffering from arthritis pain, rheumatoid join pain, back pain, muscle stiffness and headaches. The invention can also provide calming effects on the user when used at night before bedtime.

More specifically, the invention composition includes phytocannabinoids in a carrier vehicle. The carrier vehicle is preferably a combination of one or more of the following: Organic bees wax, pure African natural shea-butter and coconut oil.

Optional ingredients include essential oils such as rose oil which contains Vitamin A.

All the ingredients in the composition are good for reducing inflammation.

Another purpose of the invention is providing an alternative to prescription drugs, opioid drugs, for managing pain. Yet another purpose of the invention is to provide a lip balm to apply to the user's lips.

Another purpose of the invention is to provide a cream for applying to the user's skin.

SUMMARY OF THE INVENTION

In the present invention, these purposes, as well as others which will be apparent, are achieved generally by a composition for pain relief comprising phytocannabinoids and a carrier vehicle for the phytocannabinoids.

The phytocannabinoids are present in the compositions in a therapeutic amount to relieve pain where it is applied.

The composition is applied topically to the user's skin and/or lips to alleviate and relieve pain.

The phytocannabinoids used in the invention are selected from the group consisting of cannabidiol (CBD), and tetrahydrocanniabinol (THC).

The carrier vehicle includes beeswax and/or shea butter.

The compositions are made into a balm or a cream or ointment.

Other objects, features and advantages of the present invention will be apparent when the detailed description of the preferred embodiments of the invention are considered with reference to the drawings, which should be construed in an illustrative and not limiting sense.

DETAILED DESCRIPTION OF THE INVENTION

The invention provides a composition for pain relief comprising a therapeutic amount of phytocannabinoids in a carrier vehicle. The compositions include the two main cannabinoids, tetrahydrocannabinol (THC) and cannabidiol (CBD) as well as other cannabinoid extracts like CBG which are present in small trace amounts. The phytocannabinoids are extracted from a powder made by grinding the shake, flower, buds, small and large leaves of the marijuana plant.

The phytocannabinoids used in the invention come from shake from the marijuana plant. Shake as used in this specification refers to the "leftovers" of the marijuana plant. Essentially, shake consists of small pieces of cannabis flower that break off larger buds. Shake can contain stems and other bits of unwanted plant matter. The shake used in the invention is in a dry form.

The flower of the marijuana plant can be used in the invention as well and is added to the shake. If the flower is added, higher levels of THC, trichomes and other cannabinoids will be obtained during the extraction process.

It is noted that the larger big leaves on the marijuana plant do not contain THC but contains CBD. These larger leaves are used in medicinal and herbal healing since CBD is known to help alleviate pain as well as controlling seizures. Since there is no THC in these leaves, they do not provide a psychotic effect. For most uses these large leaves are considered waste and discarded unused, but they are part of the invention.

The shake also includes crystals or trichomes. Trichomes are left over crystals from the small flowers on the flower buds. That's the smaller leaves from the flower buds that are on the side some around it. The smaller leaves have properties as well mostly trichomes and other properties when it is extracted by the heat process. The strength of the trichomes, as well as the other cannabinoids, gets diluted when they are mixed with the shea butter and beeswax.

So, the invention uses the entire marijuana plant, shake, leaves, flower buds, flowers, small leaves and large leaves.

As with many aromatic terpenoids, THC has a very low solubility in water, but good solubility in most organic solvents, specifically lipids and alcohols.

CBD is insoluble in water but soluble in organic solvents such as pentane. At room temperature, it is a colorless crystalline solid. In strongly basic media and the presence of air, it is oxidized to a quinone. Under acidic conditions it cyclizes to THC.

The invention compositions are made by grinding the shake like coffee in a food processor until it looks like a green powder, similar to green tea.

The ground shake is added to coconut oil in a 1:1 ratio (meaning 1 cup coconut oil to 1 cup of shake) and heated to approximately 200 to 212 degrees F. for 3.5 to 4 hours. While stirring it every 5 minutes. After the extraction process is completed THC and CBD have been released as the two main compounds. Other trace amount of cannabinoids like (CBG) extract and trichomes are also present, but mostly THC and CBD.

After this time the hot liquid is passed through cheesecloth to remove large debris. The remaining extracted liquid is separated and is used to combine with the carrier vehicle to create the balm and cream of the invention.

After the extracted liquid cools off, it is left over night to set in and to solidify. It takes at least from 6 to 12 hours to set in. After 12 hours pass or the next day the liquid is heated up slowly in a double boiler, adding the unrefined 100% Natural Shea Butter (grade A) from Ghana Africa to it, along with the 100% natural bees wax, making sure all is melted together and mixed well, no clumps, keep mixing and adding together more if need it.

The carrier vehicle is preferably Shea Butter and/or beeswax, but any other similar material can be used. Generally, up to 25% of Shea Butter is present in the resulting composition. Up to 25% of beeswax is present in the resulting composition. The percentages of Shea Butter and beeswax vary depending on whether the resulting product is an ointment, balm or cream. Both the Shea Butter and beeswax are added to up to 50% of the extracted liquid containing the phytocannabinoids.

The mixture is continuously stirred until desired consistency and thickness is reached. The original liquid (the shake and coconut oil that became solid form after the 6 hours) after that while is still hot in liquid form the mixture is poured into containers adding some 100% natural essential oils for fragrance. Rose oil, eucalyptus, spearmint is the most used, but other material such as arnica oil can be used as well.

One tablespoon of cream/balm is used per dose. The active ingredient per dose of the ointment/cream/balm is 5% of THC, 5% of CBD and small traces, 1% or less, of CBG and other cannabinoids.

Typically, the effects of the invention compositions last up to 8 hours so that the ointment, cream and balm can be applied to the user up to 3 times a day.

EXAMPLE 1

A patient on opioid medication used the cream for sciatica pain. The patient was able to stop taking the opioid medication. Each patient used 2 tablespoons and sometimes 3 tablespoons of the invention cream and kept reapplying at least 3 to 4 times a day. They felt better right away after each application and when they started to feel the pain again after approximately 6 hours, they would apply one or two tablespoons and the result was always immediate. The cream includes a concentration of at least 15% of THC and 15% CBD per application, which in this case is 3 doses. The amount per one dose is 5% THC and 5% CBD.

EXAMPLE 2

A patient with arthritis pain used the invention cream. The invention cream was applied morning and night. After the morning application about 2 tablespoons was applied by the patient who then felt better for the whole day. At night 2 tablespoons of the cream was replied and the patient was relived of pain for the whole night. The cream used contained 10% of THC and 10% of CBD per application.

EXAMPLE 3

A patient with back pain used 3 tablespoons of the cream 3 times a day and applied it every 4 hours. They felt immediate relief which lasted till next day. The cream used contained 15% THC and 15% of CBD per application.

EXAMPLE 4

A patient with headaches applied a half tablespoon of the invention cream every 2 hours for 3 times. After the 3rd time of application the headache was relived. The cream concentration was 2.5% of THC and 2.5% CBD per application.

EXAMPLE 5

A patient with menstrual pain applied 2 tablespoons of the invention cream every 3 hours 4 times a day on lower abdomen. The menstrual pain was alleviated. The cream included 25% THC and 25% CBD per application.

EXAMPLE 6

A patient with breast pain applied 2 tablespoons of the invention cream and was relived after 1 hour after application. They reapplied when the pain came back after approximately 4 hours, and they reapplied again when the pain returned after approximately 4.5 hours. After 30 minutes the pain was gone for the whole evening 6 hours later. The cream was applied at night time and almost immediately within 15 minutes the patient felt better, and they slept better as well. The cream included 10% THC and 10% CBD application.

The foregoing description of various and preferred embodiments of the present invention has been provided for purposes of illustration only, and it is understood that numerous modifications, variations and alterations may be made without departing from the scope and spirit of the invention as set forth in the following claims.

What is claimed is:

1. A topical composition for pain relief comprising a phytocannabinoids liquid and a carrier vehicle;
wherein said liquid is made from a phytocannabinoids powder by grinding the shake, flower, buds, small and large leaves of the marijuana plant and mixing with coconut oil in a 1:1 ratio to create a liquid mixture; heating said mixture to a temperature between 200 to 212° F. for 3 to 4 hours, while stirring every 5 minutes to release the cannabinoids from said powder; filtering the hot mixture to remove large debris leaving said phytocannabinoids liquid which is combined with a carrier vehicle made of up to 25% shea butter and up to 25% beeswax to create the topical composition;
said phytocannabinoids are present in the composition in a therapeutic amount;
wherein said composition is delivered to a user's skin and/or lips to alleviate pain.

2. . The composition according to claim 1, wherein said phytocannabinoids are from the group consisting of cannabidiol (CBD), cannabigerol (CBG), and tetrahydrocannabinol (THC).

3. The compositions according to claim 1, wherein said carrier vehicle is a balm.

4. The composition according to claim 1, wherein said carrier vehicle is a cream.

5. The composition according to claim 1, wherein said carrier vehicle is an ointment.

6. The composition according to claim 1, further including essential oils and/or arnica oil.

7. The composition according to claim 1, wherein the resulting composition has tetrahydrocannabinol (THC) present in an amount up to 25%.

8. The composition according to claim 1, wherein the resulting composition has cannabidiol (CBD) present in an amount up to 25%.

9. The composition according to claim 1, wherein the resulting composition has cannabigerol (CBG) and other cannabinoids present in trace amounts up to 1%.

10. The composition according to claim 1, wherein the resulting composition is applied to the user to alleviate sciatica pain, arthritis pain, back pain, headaches, menstrual pain and breast pain.

11. A method of making a topical composition for pain relief comprising the steps of: grinding solid material from a marijuana plant including the shake, flower, buds, small and/or large leaves to create a powder;
adding said powder to coconut oil in a 1:1 ratio to create a liquid mixture;
heating said mixture to a temperature between 200 to 212° F. for 3 to 4 hours, while stirring every 5 minutes to release the cannabinoids from said powder;
filtering the hot mixture to remove large debris; and
combining with a carrier vehicle to create the topical composition.

12. The method according to claim 11, wherein said hot mixture is let to cool and solidify at least 6 to 12 hours.

13. The method according to claim 12, wherein said solidified mixture is slowly heated in a double boiler.

14. The method according to claim 13, wherein said carrier vehicle is shea butter and/or beeswax and is added to said mixture and is allowed to cool.

15. The method according to claim 14, wherein said shea butter and/or beeswax are present in the resulting mixture in an amount up to 25%.

16. The method according to claim 15, wherein one tablespoon of the composition is the dose used and contains active ingredients of up to 25% of tetrahydrocannabinol THC and/or cannabidiol CBD and up to 1% of cannabigerol CBG and other cannabinoids.

* * * * *